United States Patent
Rassman et al.

(10) Patent No.: US 8,062,322 B2
(45) Date of Patent: *Nov. 22, 2011

(54) METHOD AND APPARATUS FOR TRANSPLANTING A HAIR GRAFT

(75) Inventors: William R. Rassman, Marina Del Ray, CA (US); Jae P. Pak, Torrance, CA (US)

(73) Assignee: William R. Rassman, Los Angeles, CA (US)

( * ) Notice: Subject to any disclaimer, the term of this patent is extended or adjusted under 35 U.S.C. 154(b) by 2060 days.

This patent is subject to a terminal disclaimer.

(21) Appl. No.: 10/640,598

(22) Filed: Aug. 12, 2003

(65) Prior Publication Data

US 2005/0187573 A1    Aug. 25, 2005

(51) Int. Cl.
*A61B 17/34* (2006.01)
(52) U.S. Cl. .......................... 606/187; 600/566
(58) Field of Classification Search .................. 600/566, 600/567; 606/167, 184, 187, 185, 133; 604/68, 604/72, 70

See application file for complete search history.

(56) References Cited

U.S. PATENT DOCUMENTS

| | | | | |
|---|---|---|---|---|
| 4,378,019 A | * | 3/1983 | Yamada | 606/187 |
| 4,874,367 A | * | 10/1989 | Edwards | 604/72 |
| 5,352,194 A | * | 10/1994 | Greco et al. | 604/35 |
| 5,817,120 A | | 10/1998 | Rassman | 606/187 |
| 5,827,297 A | * | 10/1998 | Boudjema | 606/133 |
| 5,911,703 A | * | 6/1999 | Slate et al. | 604/68 |
| 6,059,807 A | * | 5/2000 | Boudjema | 606/187 |
| 6,461,369 B1 | | 10/2002 | Kim | 606/187 |
| 7,144,406 B2 | * | 12/2006 | Pak et al. | 606/187 |

FOREIGN PATENT DOCUMENTS

EP    1312315    5/2003

* cited by examiner

*Primary Examiner* — Victor Nguyen
(74) *Attorney, Agent, or Firm* — Haynes and Boone, LLP

(57) ABSTRACT

A hair transplant apparatus and a method for placing hair grafts into pre-made wounds capture a hair graft into a hair graft chamber readily aligned for implantation into the human scalp. The hair graft can be placed into the hair graft chamber manually or mechanically (e.g., by vacuum). A hair transplant apparatus includes a housing and a sliding rod within the housing. When the sliding rod is away from an open distal end of the housing in a first position, a hair graft can be placed into the spacing between an end of the rod and the open distal end of the housing. In a second position, the rod is advanced so the end of the rod becomes substantially flush with the distal end of the housing, thereby pushing the hair graft out of the housing and into the pre-made wound. Advantageously, the housing is aligned with the direction of the pre-made wound allowing the hair graft to slide easily into the pre-made wound without damage. Extraneous forces are eliminated by the alignment of the housing to the wound, thus creating a linear path for the hair graft to move without obstruction to finally settle in the scalp wound.

16 Claims, 14 Drawing Sheets

METHOD AND APPARATUS FOR TRANSPLANTING A HAIR GRAFT

BACKGROUND OF THE INVENTION

1. Field of Invention

This invention relates to an apparatus and method for transplanting hair grafts, and more particularly, to an apparatus and method for non-invasively implanting hair grafts into pre-made wounds.

2. Discussion of the Related Art

The transplantation of hair grafts into a human scalp is well understood. The present state of the art calls for excising a hair-rich area of the scalp, dissecting the excised scalp segment to obtain individual hair grafts for implantation, creating an implantation site in a bald or thinning area of the scalp by making wounds with a cutting instrument, and then implanting individual grafts into the prepared implantation sites after bleeding has ceased.

Current techniques for hair transplantation limits the transplant process to creating follicular units that contain one to four hairs bunched together as they are found in a normal human scalp and using these follicular units as hair grafts.

Two general classes of instruments are used by surgeons today to implant hair grafts. One class of instruments is designed to place hair grafts into pre-made wounds. Typically, one of the commercially available hair graft implantation instruments include a hollow needle within a sheath that is alternately moved between an extended position in which the needle extends beyond the sheath and a retracted position in which the needle is retracted within the sheath. In a second class of instruments, a single instrument makes a scalp wound and implants a hair graft into the freshly made wound in a rapid sequence of mechanical actions. These "percutaneous" instruments (through the intact skin), can be used to place hair grafts into pre-made sites as well.

These conventional instruments have several disadvantages. Usually, the instrument has very delicate and sensitive controls and requires fine adjustments to position the needle tip to capture a graft. The graft may then be held and oriented in a variety of directions. When the instrument advances the graft into the scalp, the mechanics of these instruments often dislodge either the graft being implanted or the grafts previously implanted in the general vicinity of the implant site before the placement of the graft is complete.

Conventional devices insert a part of the transplant apparatus into the scalp wound. For example, in U.S. Pat. No. 6,059,807, the graft is encased inside a needle which then is in turn inserted inside the scalp (i.e., both the needle and the graft are physically located inside the scalp during insertion.) In U.S. Pat. No. 6,461,369, a needle is inserted into the scalp with the graft attached to its distal end prior to the quick withdrawal of the needle. Thus, even if the graft is placed at the desired location within the wound, the graft can extrude from the wound because bleeding in the wound is reactivated by either the invasive needle penetrating into the wound as the instrument is manipulated, or other mechanical forces related to the needle going into and out of the wound.

Therefore a need exists for a method and apparatus for transplanting hair grafts that is simple and substantially non-invasive, allowing for complete hair graft implantation without the dislodging of surrounding hair grafts.

SUMMARY

According to one embodiment of the present invention, an apparatus for transplanting a hair graft is provided, including a housing having an open distal end and a rod inside the housing. An end of the rod is movable to a position along a central axis of the housing where the end of the rod is substantially flush with the open distal end of the housing, so that a loaded hair graft is delivered to a scalp wound. The apparatus also includes an actuator to move the end of the rod substantially flush with the open distal end of the housing.

According to another embodiment of the present invention, another apparatus for transplanting a hair graft is provided, including a rod inside the housing, an end of the rod being movable between a first position and a second position along a central axis of the housing. With the end of the rod in the first position, the housing provides a spacing between the end of the rod and the open distal end of the housing to receive a hair graft. With the end of the rod in the second position, the end of the rod is substantially flush with the open distal end of the housing, so that the hair graft is delivered to a scalp wound. The apparatus further includes an actuator to move the end of the rod between the first and second positions along the central axis of the housing.

According to another embodiment of the present invention, another apparatus for transplanting a hair graft is provided, including a housing having an open distal end, a first portion of the housing being separable from a second portion of the housing for loading a hair graft.

According to another embodiment of the present invention, a method for transplanting a hair graft is provided, including providing a housing having an open distal end and providing a rod inside the housing. The method further includes providing a spacing between the end of the rod and the open distal end of the housing, loading a hair graft into the spacing, and moving the end of the rod substantially flush with the open distal end of the housing thereby moving the hair graft out of the spacing and into a scalp wound without the open distal end of the housing penetrating the scalp wound.

According to another embodiment of the present invention, an apparatus for loading a hair graft ready to transplant is provided, including a housing having an open distal end, and an aperture through a side of the housing apart from the open distal end. A vacuum is operably coupled to the aperture to provide suction at the open distal end thereby drawing a hair graft into the housing through the open distal end.

According to yet another embodiment of the present invention, an apparatus for loading a hair graft ready to transplant is provided, including a first portion of a housing and a second portion of the housing separable from the first portion. A joint is included for coupling the first and second portions, wherein the coupled first and second portions provide an open distal end of the housing through which a loaded hair graft is deployable.

These and other features and advantages of the present invention will be more readily apparent from the detailed description of the embodiments set forth below taken in conjunction with the accompanying drawings.

BRIEF DESCRIPTION OF DRAWINGS

Use of the same reference symbols in different figures indicates similar or identical items. It is further noted that the drawings may not be drawn to scale.

DETAILED DESCRIPTION

Figure 1A:
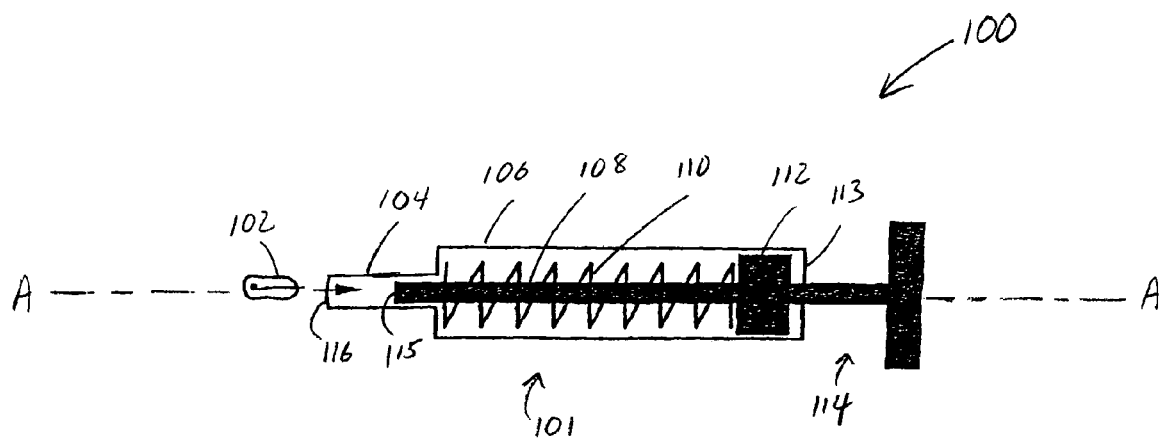
FIGS. 1A through 1D are schematic cross sections of a spring-loaded transplant apparatus showing a method for hair graft capture and implantation in various stages of operation, in accordance with one embodiment of the present invention.

In conventional hair graft transplanting instruments, a needle is in part or in whole inserted through the skin or the skin edge of a wound to a depth approximately equal to the length of a human hair follicular unit. These instruments guide the hair to its final resting position through a mechanical process where a part of the transplant instrument (e.g., a finger projection or a needle type housing) holds the graft as that part of the instrument is inserted to its ideal depth before the graft is expelled from the instrument. The part of the instrument that goes below the skin edge adds bulk to the space where the hair graft is being placed. The mechanical action of the instrument as it implants a graft places pressure on the skin, whether or not it is cutting though the skin, and also increases the volume and pressure within the space intended only for the hair graft.

The changes in the wound environment at or below the point where the graft is to be inserted is dynamic. There are volume and pressure effects within the space for the hair graft. The physical dynamics of the implanting process impacts the area below the skin by increasing the volume as a portion of the instrument is placed below the skin during implanting, and by adding additional volume as the hair graft is moved out of the instrument while the instrument is still present in the same space. Each component of the increased volume translates into an increase in pressure below the skin edge. The change in pressure is transmitted outside the confined space laterally as well as out the wound itself. Additional impacts include dilation of the skin as grafts are placed into pre-made sites, depression of the skin as the skin edge is cut with a cutting device, and reactivation of freshly made wounds from the mechanical disturbances. The mechanical disturbances cause the blood vessel to "pump" blood into the wound at systolic blood pressures levels.

All of these factors add incremental disturbances to the grafting area. As the sum of these volumes, pressures, and mechanical forces build, there is a great tendency for graft extrusion to occur during implantation, in a manner similar to a cork popping from a champaign bottle.

These forces may cause one or more of the following to occur: (a) a graft that is implanted is extruded immediately upon placement; (b) the grafts adjacent to the one that is placed are extruded; or (c) the grafts further and further from the implant site extrude (resulting from a limited "chain-reaction").

The present invention advantageously provides a method and apparatus for capturing a hair graft in a desired orientation and position, and for substantially non-invasively implanting the hair graft into a human scalp, thereby allowing for a more complete and stable implantation. The hair graft apparatus and method captures a hair graft from a supply of grafts previously extracted from an excised portion of the patient's scalp.

FIGS. 1A through 1D are schematic representations of an apparatus and method for transplanting a hair graft in accordance with an embodiment of the present invention. FIGS. 1A through 1D show hair transplant apparatus 100 in cross section.

Figure 1B:
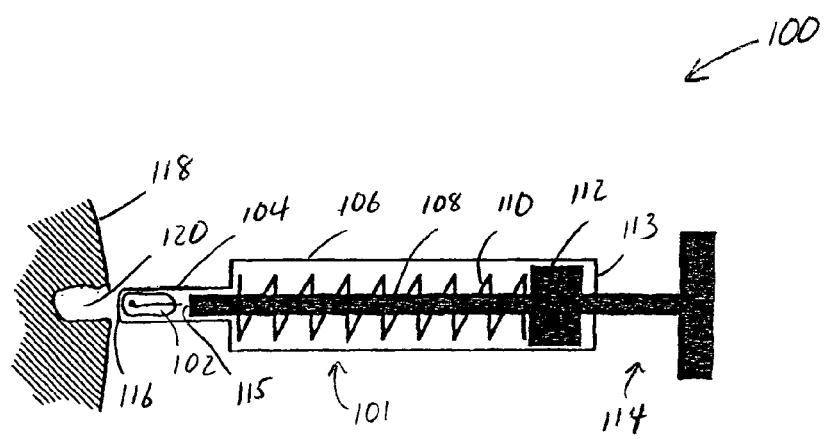
Figure 1C:
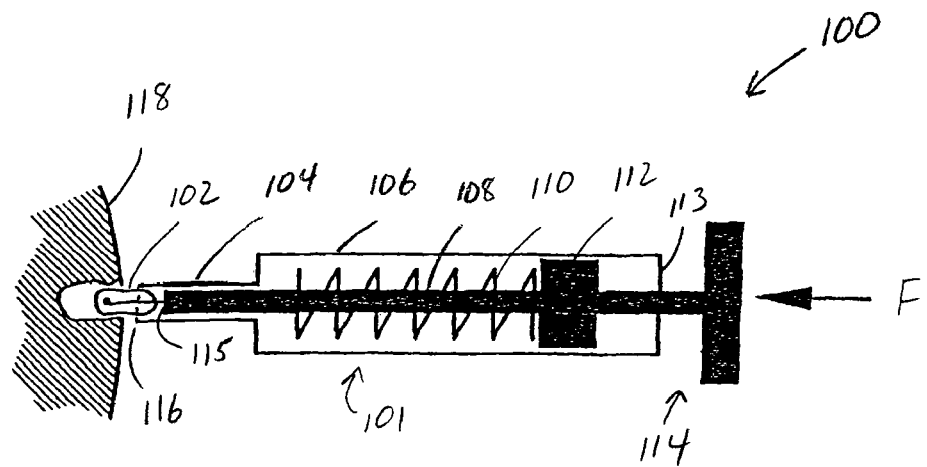
Figure 1D:
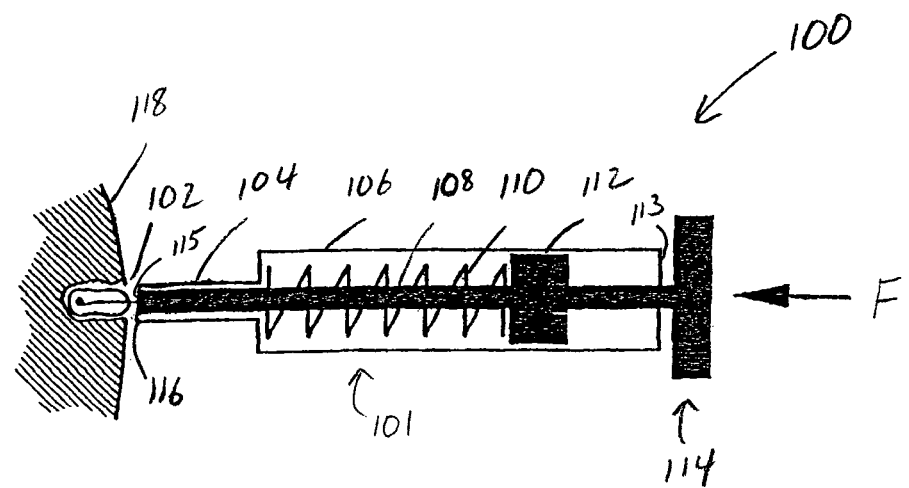
Figure 2A:
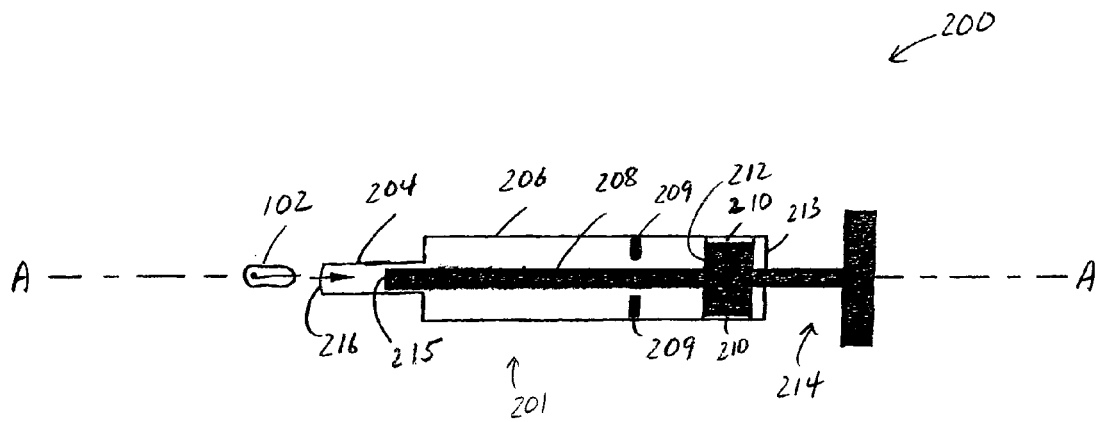
FIGS. 2A through 2D are schematic cross sections of another transplant apparatus showing a method for hair graft capture and implantation in various stages of operation, in accordance with another embodiment of the present invention.
Figure 2B:
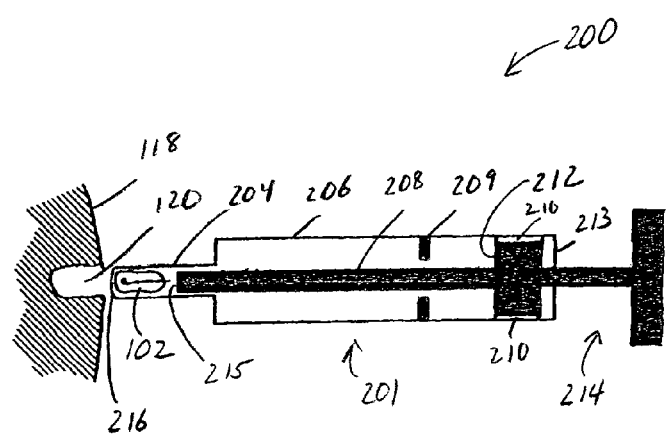
Figure 2C:
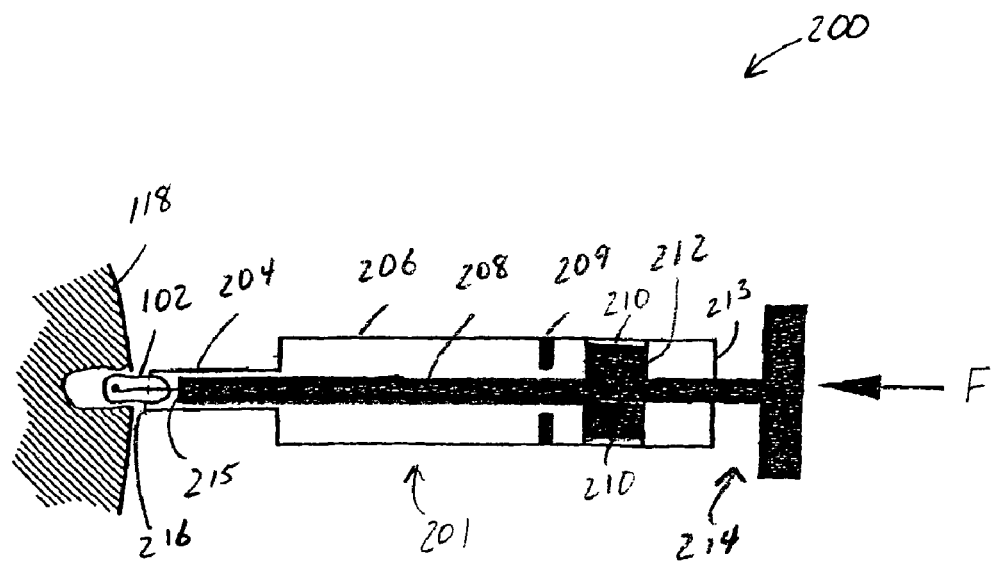
Figure 2D:
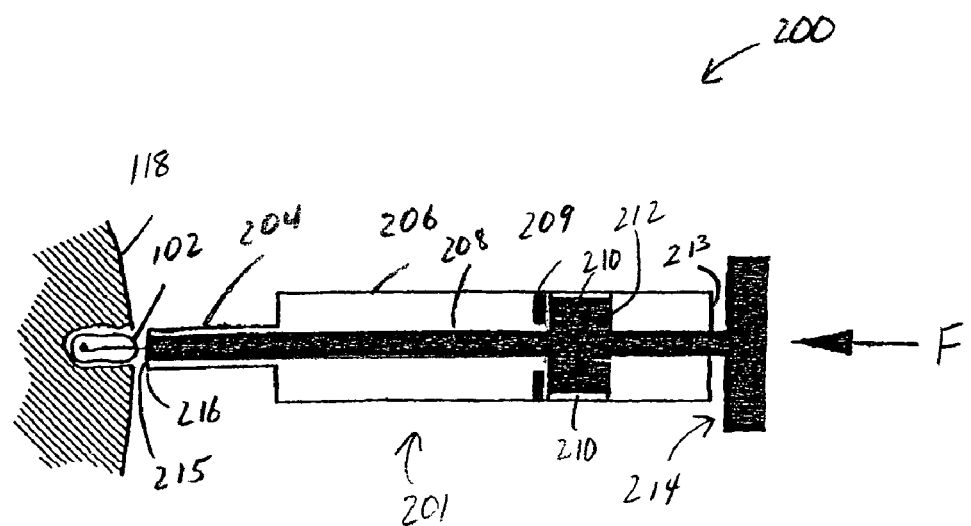

In one embodiment, hair transplant apparatus 100 includes a housing 101 having a hair graft chamber 104 and a piston chamber 106. A proximal end of hair graft chamber 104 is operably coupled to piston chamber 106. An initial step in the implantation procedure loads a hair graft 102 (or a series of hair grafts) into hair graft chamber 104, as shown in FIGS. 1A and 1B. Then apparatus 100 inserts graft 102 into a scalp 118, utilizing a plunger 114 to actuate a piston 112 and a rod 108 connected thereto, as shown in FIGS. 1B and 1D. In this embodiment, graft 102 may be manually loaded into graft chamber 104 using, for example, a pair of forceps. An end 115 of rod 108 is pushed towards an open distal end 116 of hair graft chamber 104 to thereby implant the hair graft into the scalp.

Hair graft 102 is loaded into a spacing within hair graft chamber 104 defined by end 115 of rod 108, open distal end 116 of hair graft chamber 104, and the interior wall(s) of hair graft chamber 104. Advantageously, hair graft 102 is loaded into hair graft chamber 104 properly positioned with the graft root system facing open distal end 116 of hair graft chamber 104, as shown in FIG. 1B. In one example, hair graft chamber 104 is provided as a hollow tube with an internal diameter only minimally larger than the width of the hair graft being implanted, thereby substantially holding the loaded hair graft in a proper loaded position and alignment. Accordingly, hair graft 102 is properly positioned with a known alignment (based upon the alignment of hair graft chamber 104) for subsequent implantation into a scalp.

In the present invention, the hair graft is constrained by hair graft chamber 104 from undesirable lateral excursions, as plunger 114 pushes the hair graft through distal end 116 and into the scalp wound. Hair graft chamber 104 assures that all of the forces applied are transmitted down a central axis A of housing 101. With the hair providing rigidity to the amorphous hair graft like a "skeleton", the hair graft does not buckle because hair graft chamber 104 constrains lateral movements of the hair graft, allowing the hair graft to be pushed out of hair graft chamber 104 with precision into the pre-made "quasi-tubular" scalp wound. The moist fat around the graft, which is relatively amorphous, lubricates the graft to allow the graft to slide through any clot in the wound, thus disturbing the wound minimally.

Figure 10A:
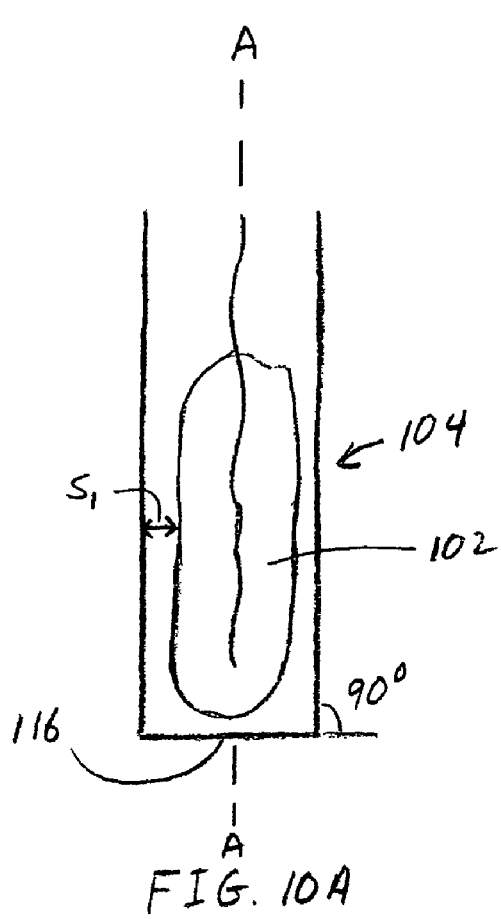
FIGS. 10A and 10B are illustrations of another loading portion of a transplant apparatus and method, in accordance with yet another embodiment of the present invention.
Figure 10B:
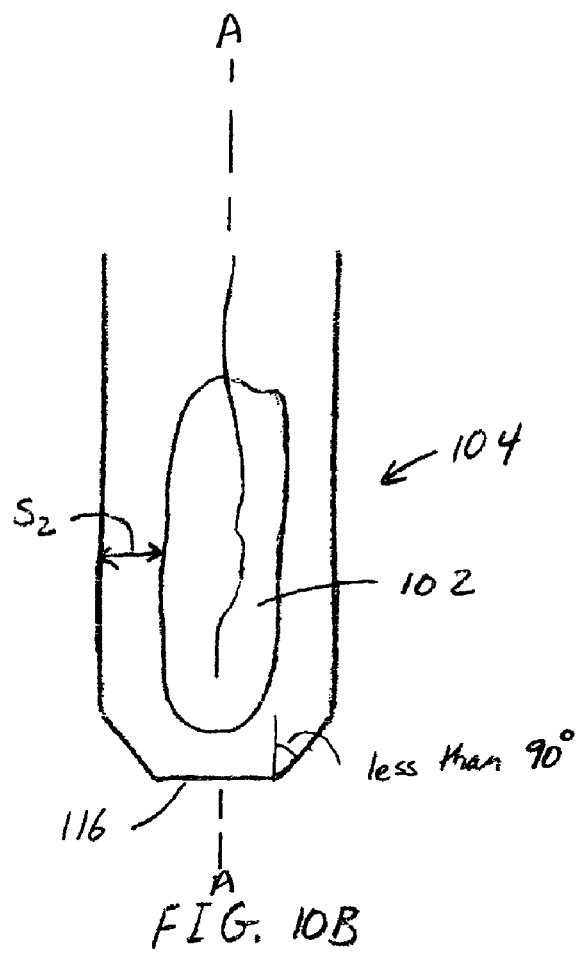

As illustrated in FIGS. 10A and 10B, if there is a significant bevel or taper at distal end 116 of hair graft chamber 104, the hair graft would tend to buckle with increasing bevel or taper angle, as the hair graft chamber's constraint on the hair graft decreases with increased taper. A slight bevel or taper at a distal end of hair graft chamber 104 can provide substantially the same function and constraint as a hair graft chamber without bevel or taper.

Referring to FIG. 10A, an example of a non-tapering hair graft chamber 104 is shown. A cross-section of distal end 116 forms a 90 degree angle with the walls of hair graft chamber 104, allowing for substantially minimum spacing $S_1$ between the surface of hair graft 102 and the inner walls of hair graft chamber 104. A non-tapered hair graft chamber 104 can thus provide increased constraints on lateral movements of the hair graft. Furthermore, a non-tapering hair graft chamber advantageously allows for the distal end of the hair graft chamber to seal on the wound opening without having to enter the space of the wound.

FIG. 10B shows an example of a tapering hair graft chamber 104. A cross-section of distal end 116 forms an angle less than 90 degrees with the walls of hair graft chamber 104, thus increasing the spacing between the surface of hair graft 102 and the inner walls of hair graft chamber 104. A typical needle has a tapered tip with an angle to the length-wise axis A of the needle ranging between about 45 to 60 degrees. Accordingly, a tapered hair graft chamber 104 provides increased spacing $S_2$ between the surface of hair graft 102 and the inner walls of hair graft chamber 104, and thereby decreases the constraints on lateral movements of the hair graft. Furthermore, in this embodiment, the tapered portion of hair graft chamber 104 would have to enter the upper aspect of the pre-made wound to form a seal at the skin edge to direct the force down the axis of the scalp wound. Disadvantageously, the further the beveled section of the tube is pushed into the wound, the more the mechanical effects of the tube's volume impact the environment around the wound such that grafts placed nearby or clots within the wound might be disturbed to reactivate bleeding.

Referring again to FIGS. 1A through 1D, piston 112 and attached rod 108 operate within piston chamber 106 and is attached to rod 108, both of which are aligned with axis A (shown by dashed lines), which is the center axis of housing 101. Rod 108 pushes hair graft 102 through open distal end 116 of hair graft chamber 104 during the implantation step. The position of end 115 of rod 108 in relation to housing 101 is important for loading the hair graft, properly positioning the loaded graft, inserting the graft into the scalp, and releasing the graft in the scalp, as will be more fully explained below. In one example, end 115 of rod 108 initially lies inside hair graft chamber 106 approximately 6 mm from distal end 116 of hair graft chamber 106. In another example, piston chamber 106 has a tubular shape and is about 2½ inches long and about ½ of an inch in diameter.

Plunger 114 is connected to piston 112 through an aperture in the proximal end 113 of piston chamber 406. Plunger 114 determines the successive positions of piston 112 and therefore also the positions of rod 108 during operation. Piston 112 and rod 108 are moved towards open distal end 116 of hair graft chamber 104 when plunger 114 is depressed with a force F, as illustrated in FIGS. 1C and 1D. Plunger 114 moves piston 112 and rod 108 towards distal end 116 along central axis A.

In this embodiment, a spring 110 is also included in piston chamber 106 between piston 112 and hair graft chamber 104. In the absence of force F on plunger 114, as illustrated in FIGS. 1A and 1B, spring 110 is not compressed and piston 112 is at a rest position. In the presence of force F, piston 112 moves toward open distal end 116 of hair graft chamber 104 along central axis A of housing 101, as shown in FIGS. 1C and 1D. Piston 112 is simultaneously biased by spring 110 towards proximal end 113 of piston chamber 106.

During operation, hair transplant apparatus 100 may be held between the thumb and the middle finger of the user. The index finger is left free to operate the apparatus as will be more fully explained hereinafter. The user may hold apparatus 100 in different ways, such as within the palm using the thumb to operate the apparatus.

After loading a hair graft into hair graft chamber 104, housing 101 is positioned over a scalp wound 120 of scalp 118, as illustrated in FIG. 1B. Hair graft chamber 104 is aligned in the direction of the aperture of the scalp wound and pressed gently against the skin. The fit between distal end 116 of hair graft chamber 104 and the open wound is snug but great care is taken not to allow distal end 116 of hair graft chamber 104 and other portions of apparatus 100 to significantly enter the wound.

Advantageously, because the hair graft is constrained within hair graft chamber 104, an operator can easily align the hair graft along hair graft chamber 104 and distal end 116 of hair graft chamber 104 with the opening in the scalp wound. The device then requires minimal coordination on the part of the operator to advance rod 108 during the actual implanting of the graft.

With a hair graft loaded inside hair graft chamber 104, distal end 116 of hair graft chamber 104 located at the skin edge, and the axis of hair graft chamber 104 placed in alignment with the axis of the wound, plunger 114 is activated, as shown in FIGS. 1C and 1D. Plunger 114 is engaged by providing force F on plunger 114 towards distal end 116, causing piston 112 and connected rod 108 to move toward distal end 116. Advantageously, an operator may apply force F using a single finger. As plunger 114 moves rod 108 toward distal end 116, end 115 of rod 108 is brought down upon the proximal end of the hair graft, and the hair graft advances out of hair graft chamber 104 along a path of least resistance into the wound, splinted by the hair(s) in the graft and constrained by the inner surface of hair graft chamber 104 surrounding the graft.

Advantageously, the housing is aligned with the direction of the pre-made wound allowing the hair graft to slide easily into the pre-made wound without damage. Extraneous forces are eliminated by the alignment of the housing to the wound, thus creating a linear path for the hair graft to move without obstruction to finally settle in the scalp wound.

Moveable rod 108 is driven by piston 112 along axis A of hair graft chamber 104 to travel the approximate length of a hair graft, so that when the implantation occurs, end 115 of rod 108 is flush with distal end 116 of hair graft chamber 104, as shown in FIG. 1D. Separation of the graft from hair graft chamber 104 is complete at the time rod 108 is fully advanced to distal end 116 of hair graft chamber 104. In one embodiment, the graft is in position inside the wound of the scalp without any portion of apparatus 100 entering the wound. In another embodiment, rod 108 may extend slightly out of the end of hair graft chamber 104 at its maximum forward position, just enough to seat the graft at or below the skin surface, but not enough to significantly enter the wound. With plunger 114 fully deployed, no significant part of apparatus 100 will be moved inside the scalp, the graft will be fully implanted, and apparatus 100 can be moved away from the skin edge with essentially no disturbance of the scalp environment.

When force F is applied to plunger 114, spring 110 is compressed between piston 112 and a distal end of piston chamber 106. In one embodiment, compressed spring 110 may be used to control the full deployment position of rod 108. The length of the fully-compressed spring 110, acting as a "stopper", will limit further movement of piston 112 and therefore rod 108. Fully deployed, end 115 of rod 108 will be substantially flush with distal end 116 of hair graft chamber 104, as shown in FIG. 1D. In other embodiments, the operator may vary the magnitude of force F applied against plunger 114 to control movement of piston 112 and rod 108. In a further embodiment, as shown in FIGS. 2A-2D, simple stoppers 209 may be provided in the interior of piston chamber 106 to physically limit the movement of piston 112, such that end 115 of rod 108 cannot extend substantially beyond distal end 116.

Piston 112 and rod 108 may be retracted by removing force F on plunger 114, thereby allowing the bias from spring 110 to move piston 112 and rod 108 toward proximal end 113 and the first rest position, as shown in FIG. 1A.

The present invention provides a hair graft transplant apparatus and method that minimizes or eliminates any part of the apparatus from entering a wound while placing grafts to a desired depth. In one embodiment, a needle (a tube with a high angled bevel) is not used, nor does the rigid tube (or minimally beveled tube) intrude significantly below the skin edge. Accordingly, the present invention reduces volumetric and pressure contributions to the scalp wound from the hair transplant instrument, thereby reducing the disturbance on existing blood clots and preventing extrusion.

FIGS. 2A through 2D are schematic representations of an apparatus and method for transplanting hair grafts in accordance with another embodiment of the present invention. FIGS. 2A through 2D show a hair transplant apparatus 200 in cross section.

Hair transplant apparatus 200 includes a housing 201 having a hair graft chamber 204 and a piston chamber 206. A proximal end of hair graft chamber 204 is operably coupled to piston chamber 206. An initial step in the implantation procedure loads hair graft 102 (or a series of hair grafts) into hair graft chamber 204. Hair graft 102 is loaded into a spacing within hair graft chamber 204 defined by end 215 of rod 208, open distal end 216 of hair graft chamber 204, and the interior wall(s) of hair graft chamber 204. Then apparatus 200 inserts graft 102 into a scalp 118 by a plunger 214 actuating a piston 212 and a connected rod 208. In this embodiment, graft 102 may be manually loaded into graft chamber 204 using, for example, a pair of forceps. An end 215 of rod 208 is pushed towards an open distal end 216 of hair graft chamber 204, thus implanting the hair graft into the scalp.

Hair graft chamber 204, piston chamber 206, rod 208, piston 212, and plunger 214 are respectively substantially similar in structure and function as hair graft chamber 104, piston chamber 106, rod 108, piston 112, and plunger 114 described above.

Apparatus 200 includes a piston ring 210 surrounding piston 212 and does not include a spring mechanism within the piston chamber. Piston ring 210 makes piston 212 fit sufficiently tight within piston chamber 206 to allow the movement of piston 212 to be more precisely controlled by the operator when applying a force F against plunger 214. In one embodiment, piston ring 210 may be formed out of rubber, a polymer, or another material having similar mechanical properties to allow for such a fit between the inner surface of piston chamber 206 and piston 212. In another embodiment, instead of including a piston ring, piston 212 may be formed out of a material that provides a fit with the inner surface of piston chamber 206 to allow the movement of piston 212 within piston chamber 206 to be precisely controlled. For example, piston 212 may be formed out of rubber, a polymer, or another material having similar mechanical properties; piston 212 may include ridges and grooves in contact with the inner surface of piston chamber 206.

Apparatus 200 may also include stoppers 209 within chamber 206 to limit the travel of piston 212 within piston chamber 206, thereby allowing a precise deployment of end 215 of rod 208 relative to distal end 216 of hair graft chamber 204.

FIGS. 3A through 3D are schematic representations of an apparatus and method for transplanting hair grafts in accordance with yet another embodiment of the present invention. FIGS. 3A through 3D show a hair transplant apparatus 300 in cross section.

Hair transplant apparatus 300 includes a housing 301 having a hair graft chamber 304 and a piston chamber 306. A proximal end of hair graft chamber 304 is operably coupled to piston chamber 306. An initial step in the implantation procedure loads hair graft 102 (or a series of hair grafts) into hair graft chamber 304. Hair graft 102 is loaded into a spacing within hair graft chamber 304 defined by end 315 of rod 308, an open distal end 316 of hair graft chamber 304, and the interior wall(s) of hair graft chamber 304.

Then apparatus 300 inserts graft 102 into a scalp 118, utilizing a vacuum apparatus 322 to actuate a piston 312 and a connected rod 308. Apparatus 300 includes vacuum apparatus 322 and ports 311 and 330 for controlling vacuum within piston chamber 306. In this embodiment, graft 102 may be manually loaded into graft chamber 304 using, for example, a pair of forceps. An end 315 of rod 308 is pushed towards open distal end 316 of hair graft chamber 304 to implant the hair graft into the scalp.

Hair graft chamber 304, piston chamber 306, rod 308, a spring 310, and piston 312 are respectively substantially similar in structure and function as hair graft chamber 104, piston chamber 106, rod 108, spring 110, and piston 112 described above.

Vacuum apparatus 322 is coupled to piston chamber 306 via port 311 to create and to release vacuum in piston chamber 306. In one example, port 311 is a simple aperture. Vacuum apparatus 322 may be any commercially available vacuum device that provides sufficient vacuum to actuate piston 312 toward distal end 316, compressing spring 310 and deploying end 316 of rod 308 to a fully deployed position. Port 330 also includes a simple aperture and a cover that can be used to open or close the aperture, to allow release or application of vacuum within piston chamber 306 (i.e., closing of port 330 applies vacuum while opening of port 330 releases vacuum). In another embodiment, a simple switch or another control mechanism is coupled to vacuum apparatus 322 to release, apply, or control the vacuum strength within piston chamber 306.

Figure 3A:
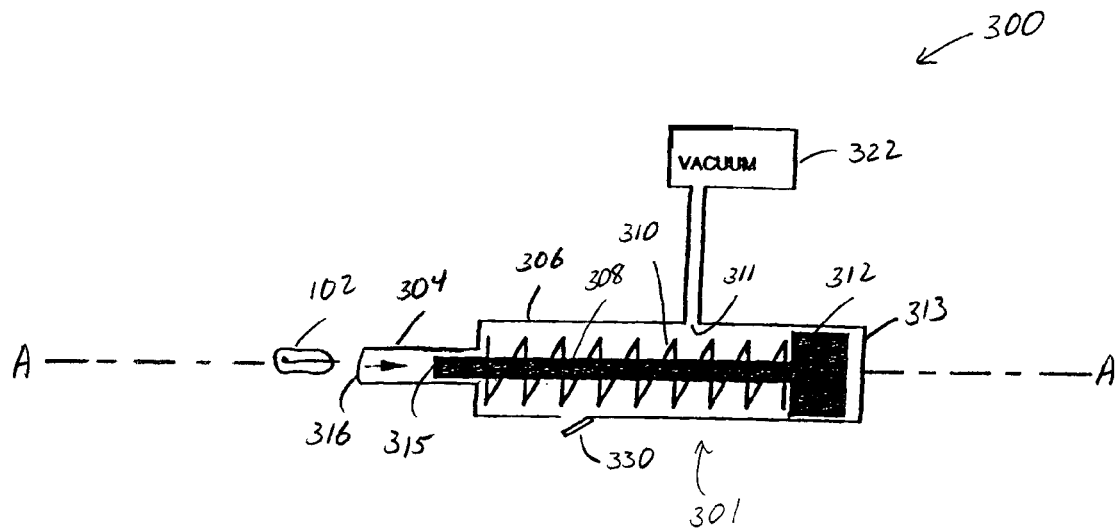
FIGS. 3A through 3D are schematic cross sections of another transplant apparatus and method including a vacuum device, in accordance with yet another embodiment of the present invention.
Figure 3B:
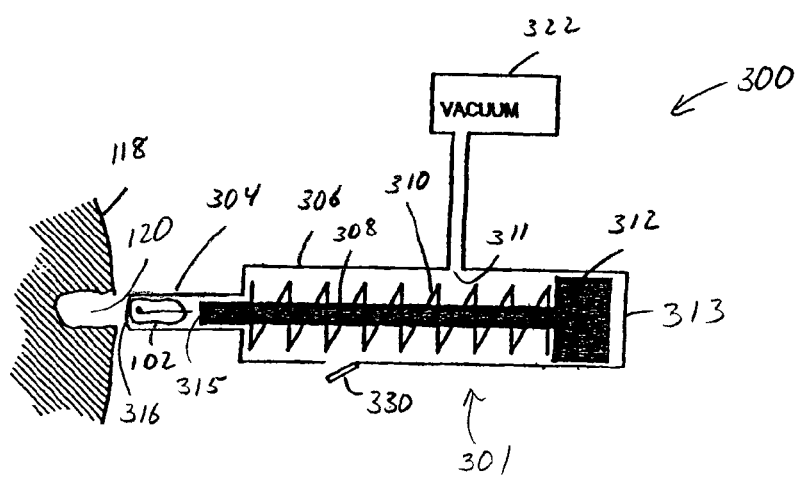
Figure 3C:
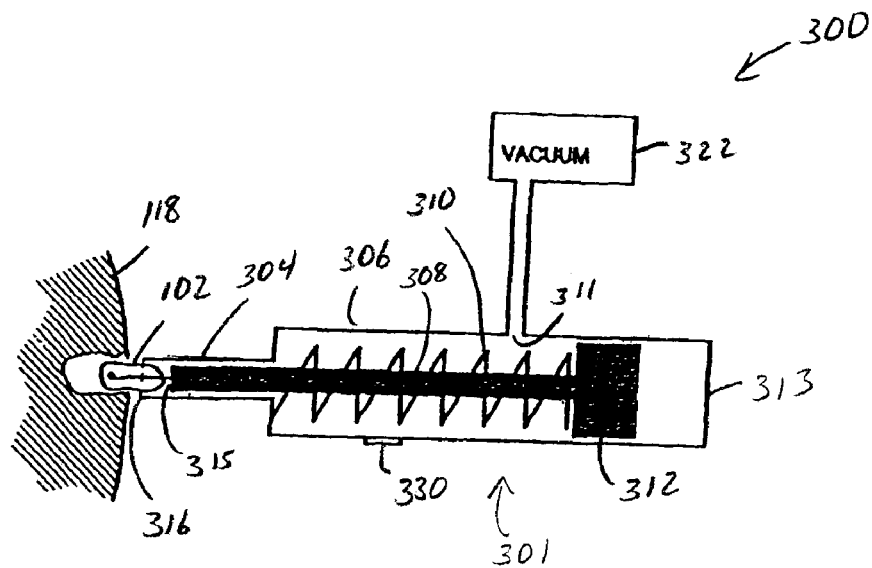
Figure 3D:
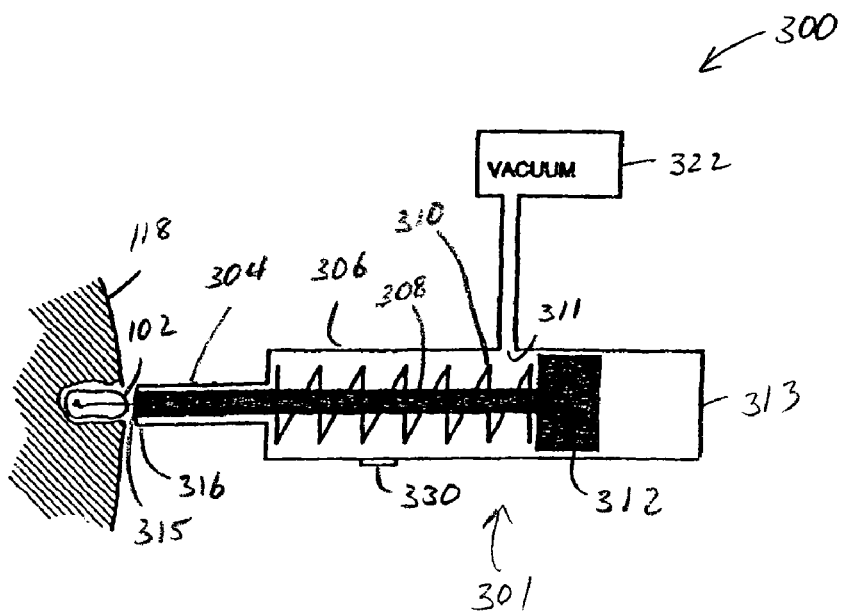

When vacuum is released in vacuum apparatus 322, as illustrated in FIGS. 3A and 3B, spring 310 is not compressed and piston 312 is at a rest position. When vacuum is applied, piston 312 moves toward open distal end 316 of hair graft chamber 304 along central axis A of housing 301, as shown in FIGS. 3C and 3D. Piston 312 is simultaneously biased by spring 310 towards proximal end 313 of piston chamber 306.

Once hair graft 102 is firmly held in the spacing of hair graft chamber 304, distal end 316 of hair graft chamber 304 is brought to an open wound 120 in scalp 118. The wound should preferably be approximately as wide as the internal diameter of hair graft chamber 304. With hair graft chamber 304 placed on the skin surface at the wound edge in an occlusive manner, and with the hair graft chamber 304 aligned with the wound from the skin edge to its depth, port 330 is closed to engage vacuum apparatus 322, thereby creating a vacuum in piston chamber 306. Accordingly, piston 312 is activated by a simple finger movement in this embodiment. Piston 312 and connected rod 308 are moved toward distal end 316 while the instrument is held still relative to the scalp. Hair graft 102 advances into the wound until the full movement of the piston and rod is complete. At this point, the graft is in its final position.

When a vacuum is created within piston chamber 306, piston 312 and connected rod 308 are driven toward distal end 316 to compress spring 310. Fully deployed, end 315 of rod 308 is substantially flush with distal end 316 of hair graft chamber 304, as shown in FIG. 3D. Compressed spring 310 may control the full deployment position of rod 308, so that end 315 of rod 308 is substantially flush with distal end 316. In another embodiment, the strength of vacuum apparatus 328 may be incrementally controlled to allow the movement of piston 312 and rod 308 to be controlled. Alternatively, stoppers may be provided in the interior of piston chamber 306 to physically limit the movement of piston 312, such that end 315 of rod 308 cannot extend substantially beyond distal end 316.

Piston 312 and rod 308 is retracted by releasing the vacuum in piston chamber 306, thereby causing spring 310 to move piston 312 and rod 308 toward proximal end 313 to the rest position, where another hair graft can be loaded, as shown in FIGS. 3A and 3B.

FIGS. 4A through 4D are schematic representations of an apparatus and method for transplanting hair grafts in accordance with yet another embodiment of the present invention. FIGS. 4A through 4D show apparatus 400 in cross section.

Hair transplant apparatus 400 includes a housing 401 having a hair graft chamber 404 and a piston chamber 406. A proximal end of hair graft chamber 404 is operably coupled to piston chamber 406. An initial step in the implantation procedure is for hair graft 102 (or a series of hair grafts) to be loaded into hair graft chamber 404. Hair graft 102 is loaded into a spacing within hair graft chamber 404 defined by end 415 of rod 408, open distal end 416 of hair graft chamber 404, and the interior wall(s) of hair graft chamber 404. A vacuum apparatus 424 is used to capture a hair graft by vacuum suction.

Then apparatus 400 inserts graft 102 into a scalp 118 utilizing a plunger 414 to actuate a piston 412 and a connected rod 408. An end 415 of rod 408 is pushed towards an open distal end 416 of hair graft chamber 404 to implant the hair graft into the scalp.

Hair graft chamber 404, piston chamber 406, rod 408, a spring 410, piston 412, and plunger 414 are respectively substantially similar in structure and function as hair graft chamber 104, piston chamber 106, rod 108, spring 110, piston 112, and plunger 114 described above.

Figure 4A:
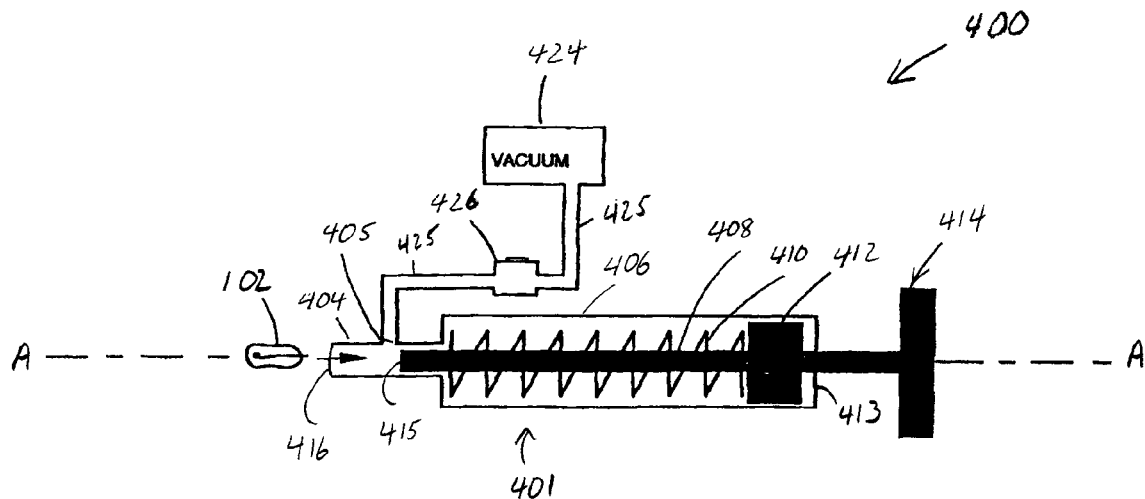
FIGS. 4A through 4D are schematic cross sections of another transplant apparatus and method including another vacuum device, in accordance with yet another embodiment of the present invention.
Figure 4B:
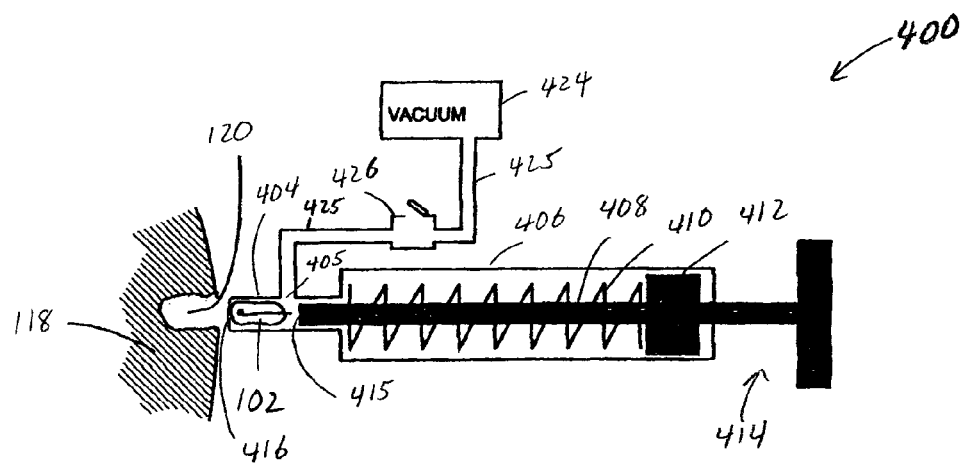
Figure 4C:
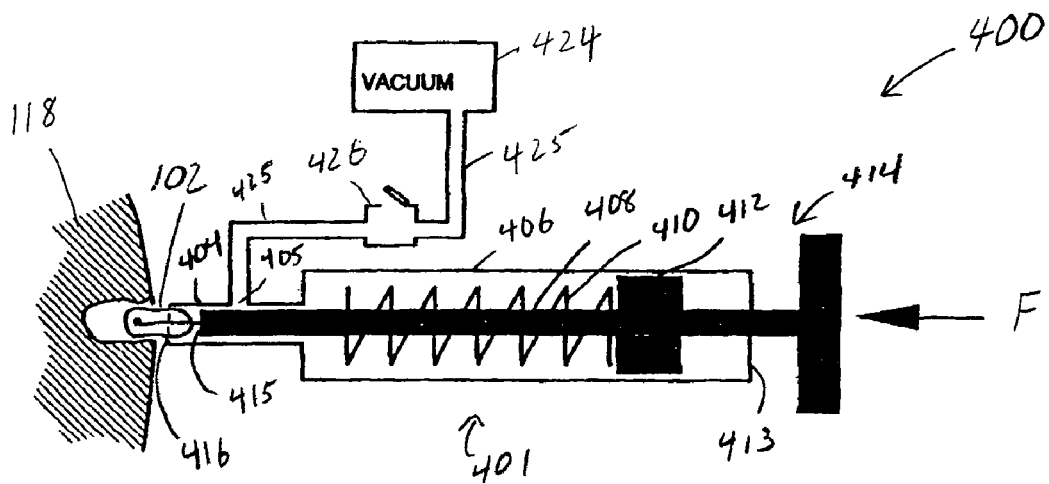
Figure 4D:
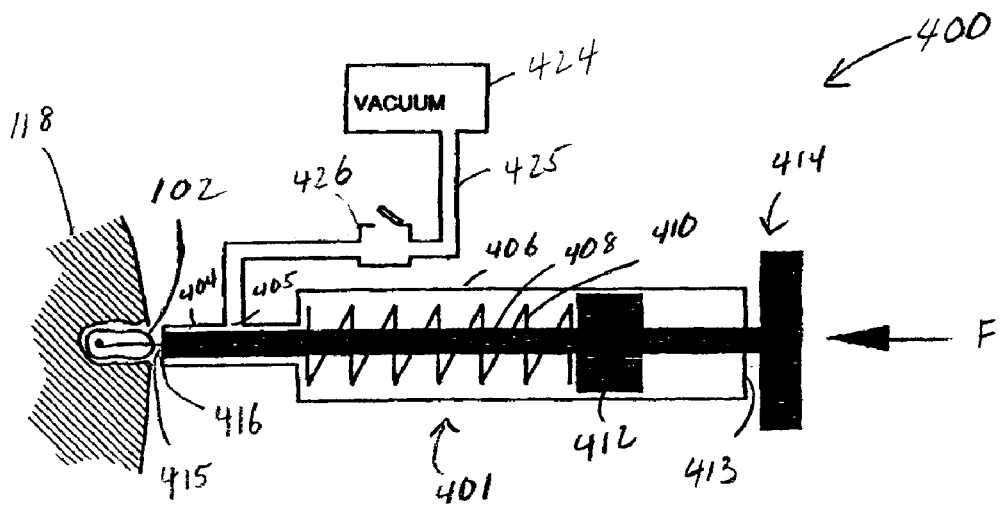

Vacuum apparatus 424, connected to a port 405 along a side of hair graft chamber 404, causes graft 102 to be drawn through an open distal end 416 of hair graft chamber 404, as shown in FIG. 4A. Vacuum apparatus 424 may be any commercially available vacuum device that provides sufficient vacuum to suction a hair graft into hair graft chamber 404. Vacuum is provided in hair graft chamber 404 through a separate tube 425 which is coupled to hair graft chamber 404 at port 405 so that suction is created at distal end 416. When the distal end of the hair graft chamber is placed against a hair graft, airflow captures the graft and then draws the graft into the hair graft chamber until the graft is stopped by end 415 of rod 408 or vacuum is released. In one example, with no intent to limit the invention thereby, end 415 of rod 408 initially lies inside hair graft chamber 404 approximately 6 mm from distal end 416 of the hair graft chamber.

A control element 426 is used to control the application and release of vacuum in hair graft chamber 404. In one example, with no intent to limit the invention thereby, control element 426 is a simple cover over an aperture along line 425 connecting vacuum apparatus 424 to port 405. Vacuum is present when control element 426 is engaged (e.g., when the cover is over the aperture) and not present when control element 426 is disengaged (e.g., when the cover is not over the aperture. In other embodiments, engaging control element 426 may release vacuum while disengaging control element 426 may apply vacuum. In another embodiment, a simple switch or another control mechanism is coupled to vacuum apparatus 424 to release, apply, or control the vacuum strength within hair graft chamber 404.

In this embodiment, apparatus 400 is conveniently hand operated and serves to load hair graft 102 into hair graft chamber 404 properly positioned. Advantageously, the hair bearing end of the hair graft is drawn into hair graft chamber 404 with the hair root system facing open distal end 416, thereby loading the hair graft in proper position and with known alignment for subsequent implantation. After hair graft chamber 404 is properly loaded, vacuum apparatus 424 is disengaged.

FIGS. 5A through 5D are schematic representations of an apparatus and method for transplanting hair grafts in accordance with another embodiment of the present invention. FIGS. 5A through 5D show apparatus 500 in cross section.

Hair transplant apparatus 500 combines the two embodiments described above with respect to apparatus 300 and 400 and illustrated in FIGS. 3A through 3D and 4A through 4D, respectively. Hair transplant apparatus 500 includes a housing 501 having a hair graft chamber 504 and a piston chamber 506. A proximal end of hair graft chamber 504 is operably coupled to piston chamber 506. An initial step in the implantation procedure is for hair graft 102 (or a series of hair grafts) to be loaded into hair graft chamber 504. Hair graft 102 is loaded into a spacing within hair graft chamber 504 defined by end 515 of rod 508, open distal end 516 of hair graft chamber 504, and the interior wall(s) of hair graft chamber 504. A vacuum apparatus 524 is used to capture a hair graft by vacuum suction.

Then apparatus 500 operates to insert the graft into the scalp utilizing piston chamber 506 to actuate a rod 508. A vacuum apparatus 522 is used to actuate rod 508 to insert the hair graft into the scalp.

Hair graft chamber 504, piston chamber 506, rod 508, spring 510, and piston 512 are respectively substantially similar in structure and function as hair graft chamber 104, piston chamber 106, rod 108, spring 110, and piston 112 described above. Vacuum apparatus 522, port 511, and port 530 are respectively substantially similar in structure and function as vacuum apparatus 322, port 311, and port 330 described above. Vacuum apparatus 524, control element 526, and port 505 are respectively substantially similar in structure and function as vacuum apparatus 424, control element 426, and port 405 described above.

Figure 5A:
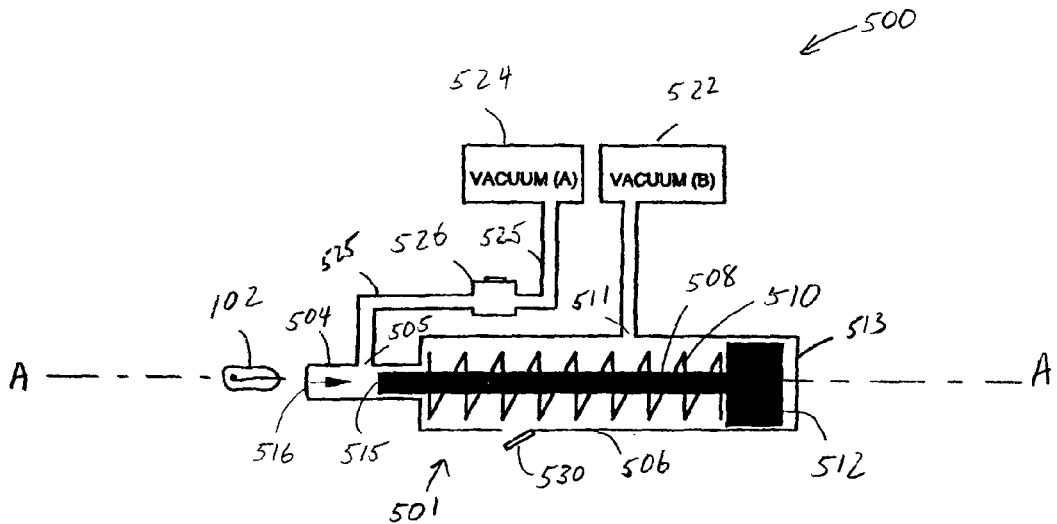
FIGS. 5A through 5D are schematic cross sections of another transplant apparatus and method including two vacuum devices, in accordance with yet another embodiment of the present invention.
Figure 5B:
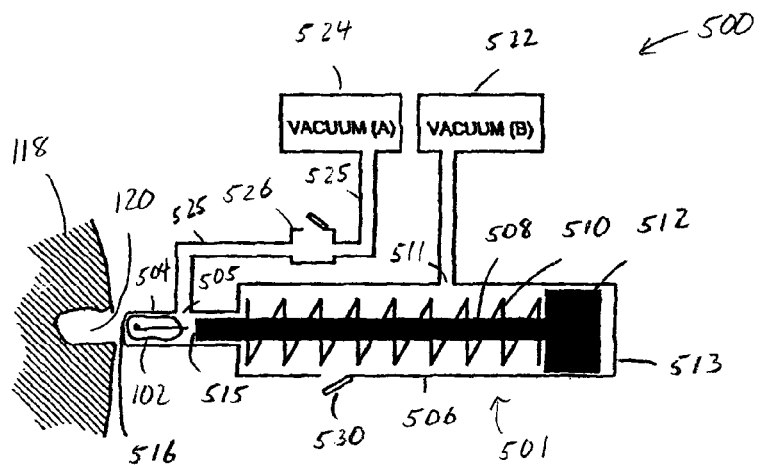

Vacuum apparatus 524, connected to port 505 along a side of hair graft chamber 504, causes graft 102 to be drawn through open distal end 516 of hair graft chamber 504, as shown in FIGS. 5A and 5B. Control element 526 is used to control the application and release of vacuum in hair graft chamber 504. When hair graft chamber 504 is properly loaded with a hair graft, vacuum apparatus 524 may then be disengaged. Advantageously, vacuum is provided by a simple movement of the operator's finger to engage or disengage control element 526. In other embodiments, a simple switch or another control mechanism is coupled to vacuum apparatus 524 to release, apply, or control the vacuum strength within hair graft chamber 504. Vacuum is subsequently applied to piston chamber 506.

Figure 5C:
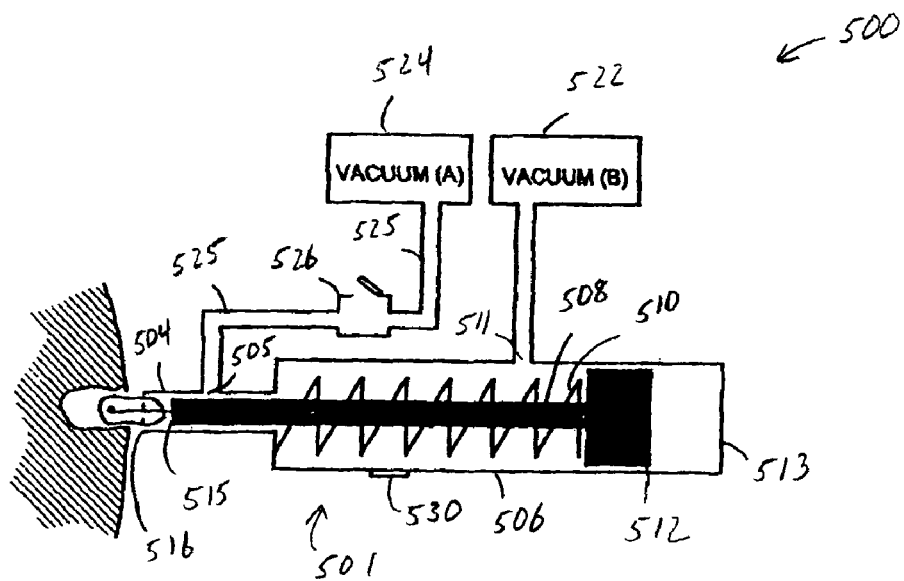
Figure 5D:
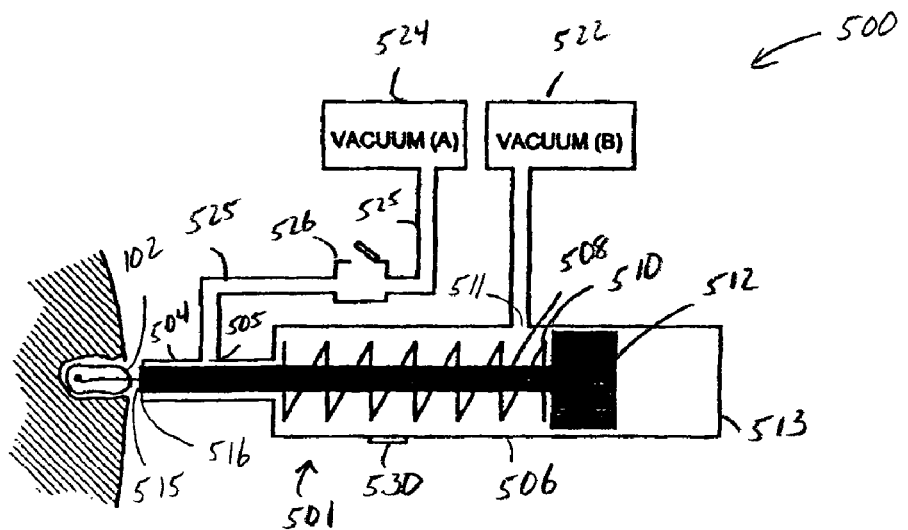

When vacuum is released from vacuum apparatus 522, as illustrated in FIGS. 5A and 5B, spring 510 is not compressed and piston 512 is at a first rest position. When vacuum is applied to piston chamber 506, as shown in FIGS. 5C and 5D, piston 512 moves toward open distal end 516 of hair graft chamber 504 along central axis A of housing 501. Advantageously, the vacuum is provided by a simple movement of the operator's finger to engage or disengage port 530. In other embodiments, a simple switch or another control mechanism is coupled to vacuum apparatus 522 to release, apply, or control the vacuum strength within piston chamber 506.

The application of vacuum within piston chamber 506 drives piston 512 and connected rod 508 toward distal end 516 and compresses spring 510. Piston 512 is simultaneously biased by spring 510 towards proximal end 513 of piston chamber 506. Fully deployed, end 515 of rod 508 is substantially flush with distal end 516 of hair graft chamber 504, as shown in FIG. 5D. Compressed spring 510 may control the full deployment position of rod 508 so that end 515 of rod 508 will be substantially flush with distal end 516. In other embodiments, the strength of vacuum apparatus 522 may be incrementally controlled to allow the movement of piston 512 and rod 508 to be controlled. Alternatively, stoppers may be provided in the interior of piston chamber 506 to physically limit the movement of piston 512, such that end 515 of rod 508 cannot extend substantially beyond distal end 516.

Piston 512 and rod 508 are retracted by releasing the vacuum in piston chamber 506, thereby causing spring 510 to move piston 512 and rod 508 toward proximal end 513 to the rest position, where another hair graft can be loaded, as shown in FIGS. 5A and 5B.

Figure 6A:
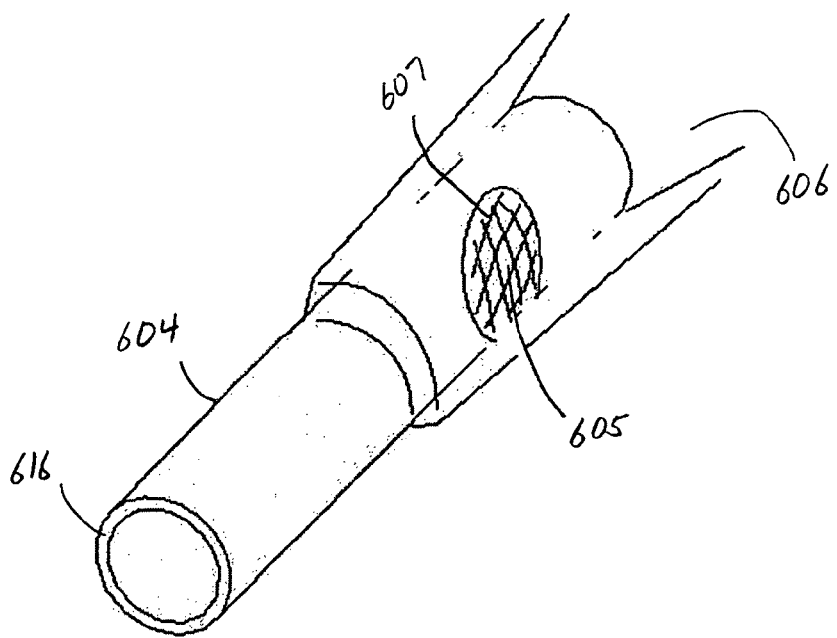
FIGS. 6A and 6B are illustrations of a loading portion of a transplant apparatus and method, in accordance with yet another embodiment of the present invention.
Figure 6B:
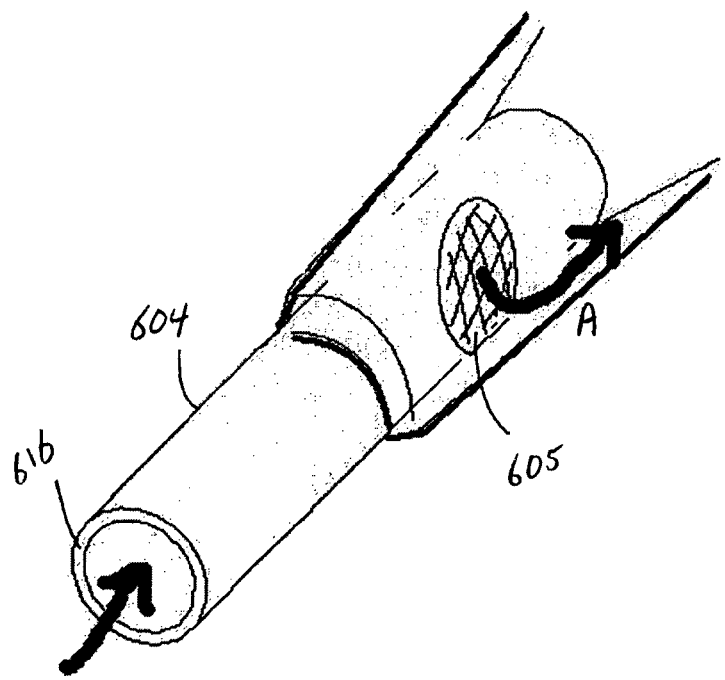

In accordance with an embodiment of the present invention, FIGS. 6A and 6B illustrate an apparatus and method for applying and releasing vacuum in a hair graft chamber as shown in FIGS. 4A through 4D and 5A through 5D.

A port 605 is provided on a side of a hair graft chamber 604 from which a vacuum apparatus, such as vacuum apparatus 424 or 524 described above, may be connected thereto by a communication means, such as tube 425 or 525 and/or control element 426 or 526. In one example, port 605 is an aperture on a sidewall of hair graft chamber 604 and includes a mesh 607 that allows air to pass but does not allow a hair graft to pass therethrough.

When the vacuum apparatus is activated to provide air suction through port 605 and accordingly through hair graft chamber 604, as illustrated by arrow A in FIG. 6B, air suction is provided at an open distal end 616 of hair graft chamber 604, as illustrated by arrow B in FIG. 6B. The air suction at distal end 616 causes a hair graft to be drawn through distal end 616 and into hair graft chamber 604, loaded and ready for implanting.

FIGS. 7A-7B, 8A-8B, and 9A-9B illustrate different embodiments of a hair graft chamber in accordance with the present invention. Each of the embodiments include a tubular hair graft chamber. Two portions of the hair graft chamber can be separated from one another for loading a hair graft. The two portions of the hair graft chamber can then be coupled together to form a hollow tube around the loaded hair graft to ready and align the hair graft for implanting into a scalp. In one example, the two portions of the hair graft chamber are halves of the tube. In a further example, the hollow tube has an internal diameter only minimally larger than the width of the hair graft being loaded.

Figures 7A, 7B:
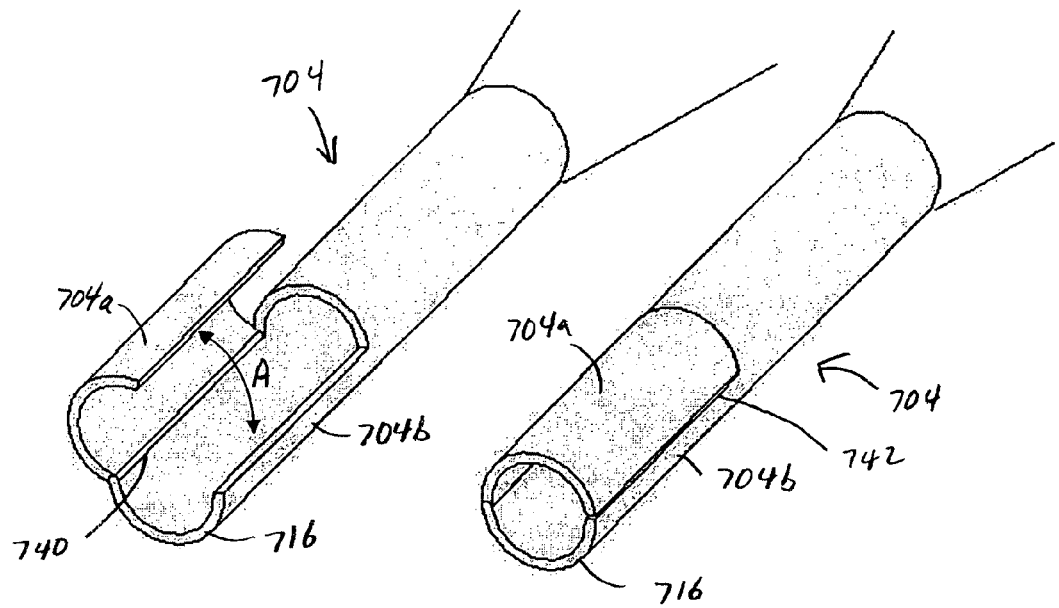
FIGS. 7A and 7B are illustrations of another loading portion of a transplant apparatus and method, in accordance with yet another embodiment of the present invention.

Referring now to FIGS. 7A and 7B, a hair graft chamber 704 is shown, including a distal end 716, a first portion 704a, and a second portion 704b. First portion 704a is movable relative to second portion 704b along an interface 740 and is coupled together along an interface 742. In one example, interface 740 may include a hinge mechanism for allowing movement of first portion 704a along directions illustrated by double-arrowed line A. In other embodiments, interfaces 740 and 742 may include other applicable joints (e.g., flexible polymer) that allow for movement of first portion 704a between an opened position, in which the two portions are separated from one another, and a closed position, in which the two portions are coupled together.

In an opened position, first portion 704a is separated from second portion 704b and a hair graft may be loaded into second portion 704b. First portion 704a is then coupled to second portion 704b to surround the hair graft with the walls of hair graft chamber 704, thereby constraining the hair graft in proper alignment for subsequent implantation by movement out of coupled hair graft chamber 704 through open distal end 716.

Figures 8A, 8B:
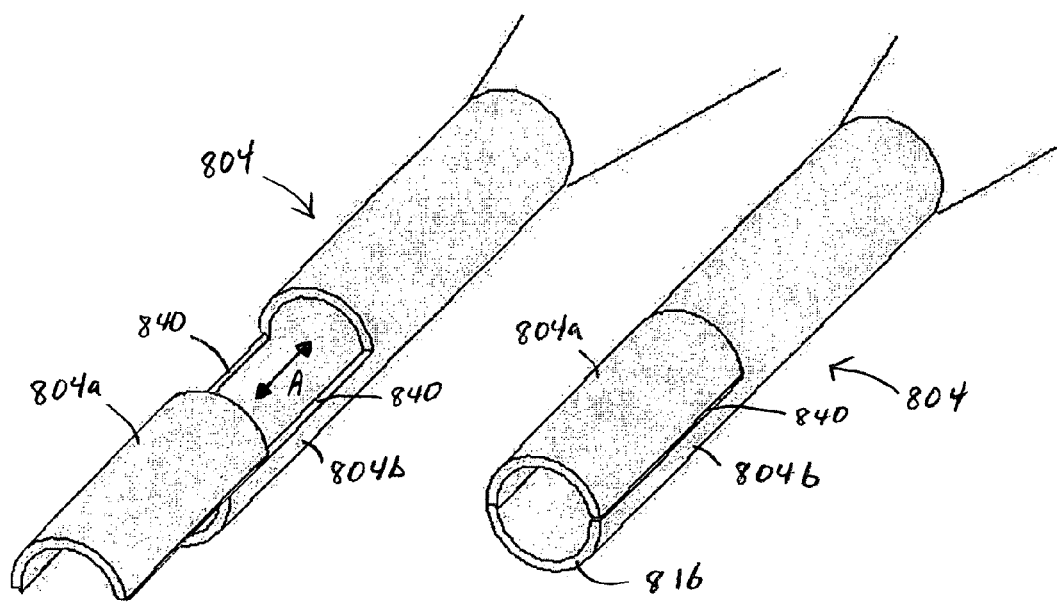
FIGS. 8A and 8B are illustrations of another loading portion of a transplant apparatus and method, in accordance with yet another embodiment of the present invention.

FIGS. 8A and 8B show a hair graft chamber 804 including a distal end 816, a first portion 804a, and a second portion 804b. First portion 804a is movable relative to second portion 804b along interfaces 840. In one example, interfaces 840 may include a sliding mechanism or joint, such as groove and coupling ridge portions, for allowing movement of first portion 804a along directions illustrated by double-arrowed line A. In other embodiments, interfaces 840 may include other applicable joints that allow for sliding movement of first portion 804a between an opened position, in which the two portions are separated from one another, and a closed position, in which the two portions are coupled together.

Figures 9A, 9B:
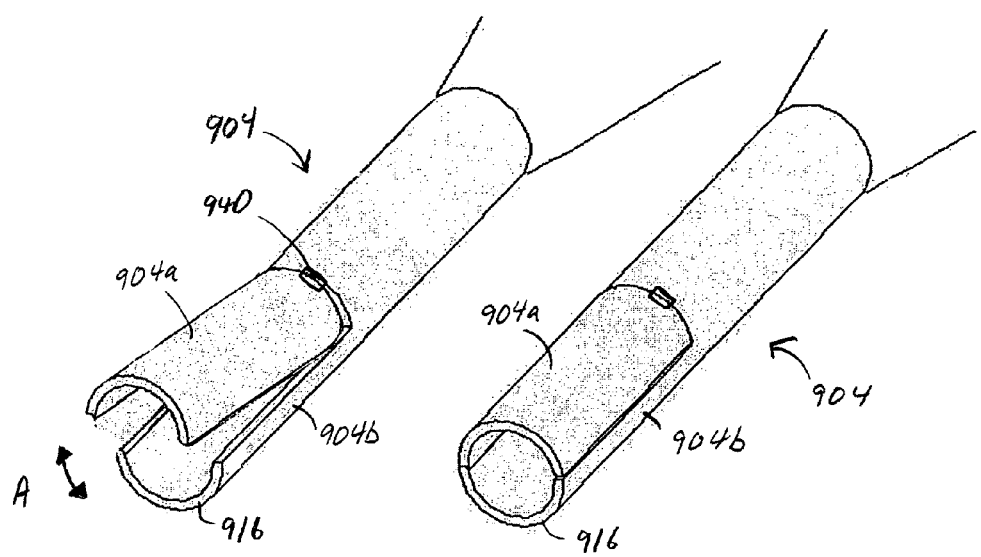
FIGS. 9A and 9B are illustrations of another loading portion of a transplant apparatus and method, in accordance with yet another embodiment of the present invention.

FIGS. 9A and 9B show a hair graft chamber 904 including a distal end 916, a first portion 904a, and a second portion 904b. First portion 904a is movable relative to second portion 904b along a joint 940. In one example, joint 940 may include a hinge mechanism for allowing movement of first portion 904a along directions illustrated by double-arrowed line A. In other embodiments, joint 940 may include other applicable joints (e.g., universal joints, ball-and-socket joints) that allow for movement of first portion 904a between an opened position, in which the two portions are separated from one another, and a closed position, in which the two portions are coupled together.

Although the embodiments illustrated in FIGS. 7A-7B, 8A-8B, and 9A-9B show interfaces between the portions of the hair graft chamber extending along only a portion of the length of the hair graft chamber, the interfaces between the two portions may also extend the entire length of the hair graft chamber. Furthermore, although the embodiments illustrated in FIGS. 7A-7B, 8A-8B, and 9A-9B show the two portions of the hair graft chamber being connected along an interface and/or joint, in one embodiment, the two portions may be completed separated from one another in the opened position for loading a hair graft. The two portions may then be coupled together for subsequent implantation of the loaded hair graft. In one example, the portions of a hair graft chamber may be connected to the free ends of a pair of forceps or arms of a tong-like structure. The portions are completely separated from one another when the forceps or arms of the tong-like structure are separated from one another. The portions are coupled together to form the tubular hair graft chamber when the forceps or arms of the tong-like structure are moved toward one another.

In another embodiment, the hair graft chamber includes a finger projection which extends beyond the distal end of the hair graft chamber along the central axis of the housing. The finger projection extends approximately the length of a hair graft. When used in this embodiment, the finger projection is placed into the wound along the axis of the wound to help direct the alignment of the apparatus when implanting the hair graft. Advantageously, the finger projection not only guides a hair graft into the wound, but it also may serve, ever so slightly, to open the wound prior to implanting the hair graft.

In a further embodiment, the rod within the piston chamber may include a finger projection extending from a free end of the rod that comes in contact with the hair graft to be implanted. Such a finger projection is disclosed in U.S. Pat. No. 5,817,120, issued to William Rassman, and is incorporated by reference herein for all purposes.

The above-described embodiments of the present invention are merely meant to be illustrative and not limiting. Various changes and modifications may be made without departing from this invention in its broader aspects. Accordingly, the invention is not limited to particular structures or dimensions. For example, the present invention can be applied to all types of hair grafts and not only the individual follicular units. In a further example, the piston described above is not limited to a mechanical part but may include a body of water or air that is movable to provide actuation of a coupled rod. Therefore, the appended claims encompass all such changes and modifications as falling within the scope of this invention.

What is claimed is:

1. An apparatus for transplanting a hair graft, comprising:
a housing having a distal end with an opening;
a rod inside the housing, an end of the rod being movable between a first position and a second position along a central axis of the housing, wherein, with the end of the rod in the first position, the housing provides a spacing between the end of the rod and the open distal end of the housing to receive a hair graft, and wherein, with the end of the rod in the second position, the end of the rod is limited to being substantially flush with the open distal end of the housing, so that the hair graft is delivered through the distal end opening to a scalp wound;
a vacuum apparatus operably coupled to the housing and configured to load the hair graft into the spacing through the distal end opening; and
an actuator configured to move the end of the rod between the first and second positions along the central axis of the housing, wherein the end of the rod lies inside a hair graft chamber.

2. The apparatus of claim 1, wherein the housing includes a piston chamber.

3. The apparatus of claim 2, further comprising means for communicating with a side aperture in the hair graft chamber for creating a vacuum within the hair graft chamber.

4. The apparatus of claim 2, wherein the actuator includes a piston inside the piston chamber.

5. The apparatus of claim 4, wherein the actuator includes a plunger connected to the piston.

6. The apparatus of claim 4, wherein the actuator includes a biasing spring operably coupled to the piston.

7. The apparatus of claim 6, wherein the biasing spring moves the end of the rod to the first position from the second position.

8. The apparatus of claim 4, wherein the piston includes a body of water or air.

9. The apparatus of claim 1, wherein the actuator includes a plunger connected to the rod, the plunger being able to move the end of the rod to the first position from the second position or to the second position from the first position.

10. A method for transplanting a hair graft, comprising:
providing a housing having a distal end with an opening;
providing a rod inside the housing, an end of the rod being movable between a first position and a second position along a central axis of the housing, wherein the end of the rod lies inside a hair graft chamber;
providing a spacing between the end of the rod and the open distal end of the housing;
vacuum loading a hair graft into the spacing through the distal end opening; and
moving the end of the rod to a limit substantially flush with the open distal end of the housing thereby moving the hair graft out of the spacing through the distal end opening and into a scalp wound without the open distal end of the housing penetrating the scalp wound.

11. The method of claim 10, further comprising moving the hair graft out of the spacing and into a scalp without the end of the rod penetrating the scalp wound.

12. The method of claim 10, further comprising aligning the hair graft with a direction of the scalp wound prior to moving the hair graft out of the spacing.

13. The method of claim 10, further comprising limiting the movement of the end of the rod with a spring.

14. An apparatus for loading a hair graft ready to transplant, comprising:
a housing having a distal end with an opening;
an aperture through a side of the housing apart from the open distal end;
a vacuum operably coupled to the aperture to provide suction at the open distal end thereby drawing a hair graft into the housing through the distal end opening; and
a rod inside the housing, an end of the rod being movable between a first position and a second position along a central axis of the housing, wherein, with the end of the rod in the first position, the housing provides a spacing between the end of the rod and the open distal end of the housing to receive a hair graft, and wherein, with the end of the rod in the second position, the end of the rod is limited to being substantially flush with the open distal end of the housing, so that a loaded hair graft is delivered through the distal end opening to a scalp wound, wherein the end of the rod lies inside a hair graft chamber.

15. The apparatus of claim 14, further comprising a communicating means coupling the vacuum and the aperture.

16. The apparatus of claim 14, further comprising a control element operably coupled to the vacuum.

* * * * *